(12) United States Patent
Teucher et al.

(10) Patent No.: US 8,956,332 B2
(45) Date of Patent: Feb. 17, 2015

(54) DRUG DELIVERY DEVICE

(75) Inventors: Axel Teucher, Frankfurt am Main (DE); Axel Forstreuter, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 58 days.

(21) Appl. No.: 13/384,036

(22) PCT Filed: Jul. 5, 2010

(86) PCT No.: PCT/EP2010/059542
§ 371 (c)(1),
(2), (4) Date: Feb. 15, 2012

(87) PCT Pub. No.: WO2011/006788
PCT Pub. Date: Jan. 20, 2011

(65) Prior Publication Data
US 2012/0136317 A1    May 31, 2012

(30) Foreign Application Priority Data
Jul. 14, 2009   (EP) .................................... 09009132

(51) Int. Cl.
*A61M 5/00*    (2006.01)
*A61M 5/315*   (2006.01)

(52) U.S. Cl.
CPC ................................ *A61M 5/31555* (2013.01)
USPC ....................................................... 604/207

(58) Field of Classification Search
USPC .......................... 604/207–211, 218, 224, 246
See application file for complete search history.

(56) References Cited

U.S. PATENT DOCUMENTS

| | | | |
|---|---|---|---|
| 7,396,347 B2 | 7/2008 | Hjertman et al. | |
| 2004/0236285 A1* | 11/2004 | Fisher et al. | 604/207 |
| 2012/0010575 A1* | 1/2012 | Jones et al. | 604/211 |

FOREIGN PATENT DOCUMENTS

| | | |
|---|---|---|
| DE | 102005019428 | 10/2006 |
| EP | 0594349 | 4/1994 |
| EP | 1923084 | 5/2008 |
| EP | 2123317 | 11/2009 |
| WO | 97/36625 | 10/1997 |
| WO | 99/38554 | 8/1999 |

OTHER PUBLICATIONS

European Search Report for European Application No. 09009132, dated Dec. 17, 2009.
International Search Report for International Pub. No. PCT/EP2010/059542, completed Oct. 12, 2010.
International Preliminary Report on Patentability for International App. No. PCT/EP2010/059542, issued Jan. 17, 2012.

* cited by examiner

*Primary Examiner* — Theodore Stigell
(74) *Attorney, Agent, or Firm* — McDonnell Boehnen Hulbert & Berghoff LLP

(57) ABSTRACT

A drug delivery device for dispensing of a dose of a medicinal product comprises a housing having a proximal end and a distal end, a container of medicinal product having a piston retained within, and a push-pull element, where the push-pull element is displaceable in proximal direction for setting of a dose and is displaceable in distal direction for dispensing of a dose. The drug delivery device may further include a piston rod coupled with the housing and with the push-pull element and coupling elements for converting a proximal displacement of the push-pull element into a rotational movement of the piston rod and for converting a distal displacement of the push-pull element into an axial movement of the piston rod with respect to the housing.

15 Claims, 13 Drawing Sheets

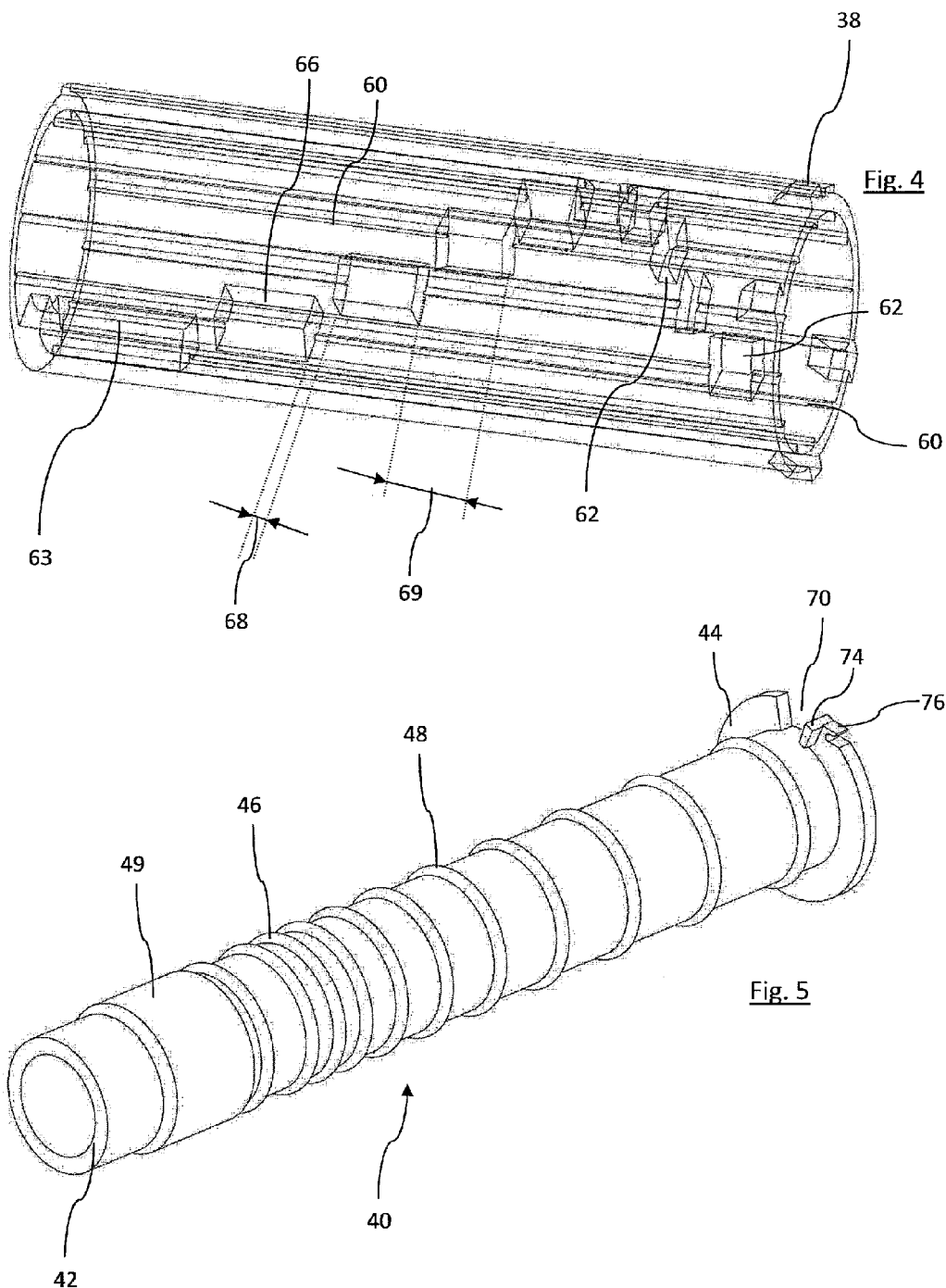

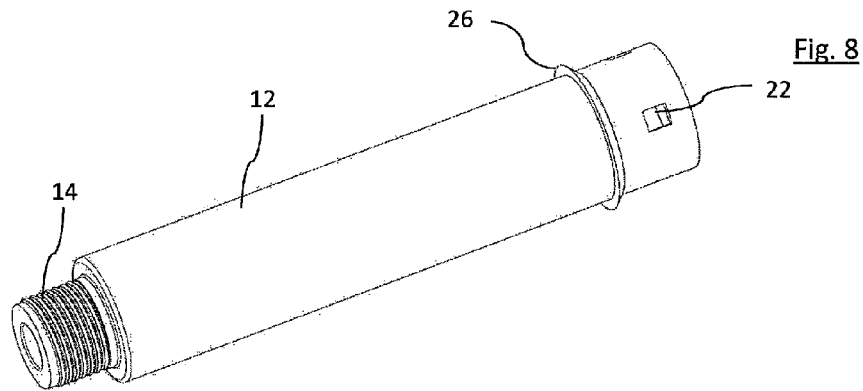
Fig. 8
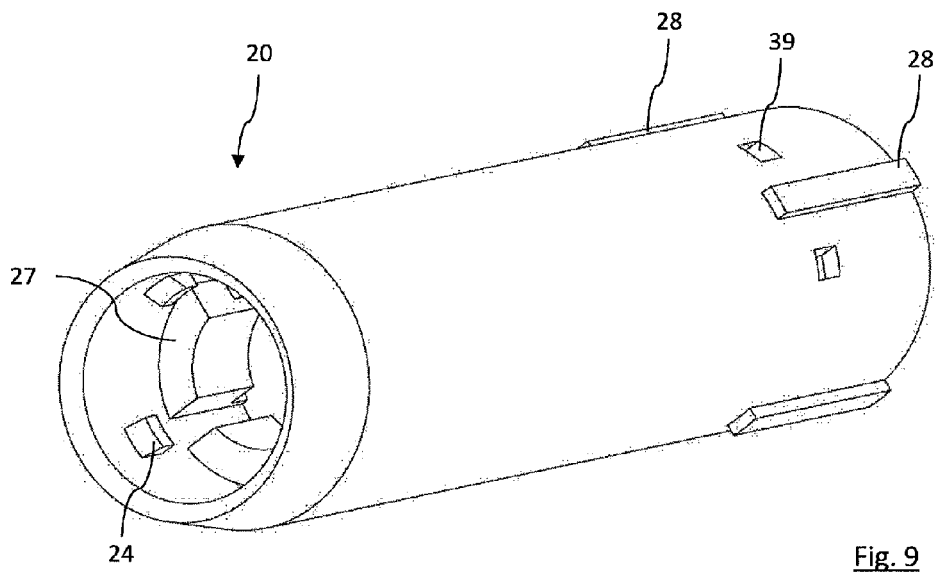
Fig. 9
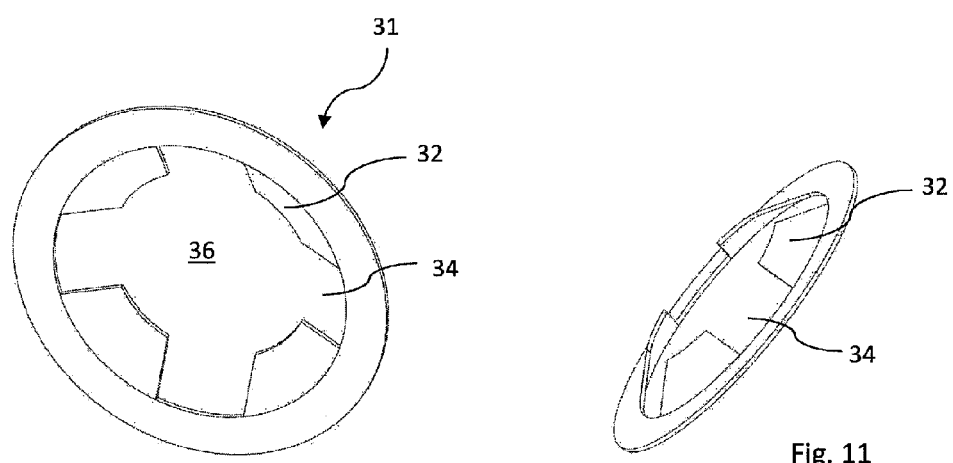
Fig. 10
Fig. 11

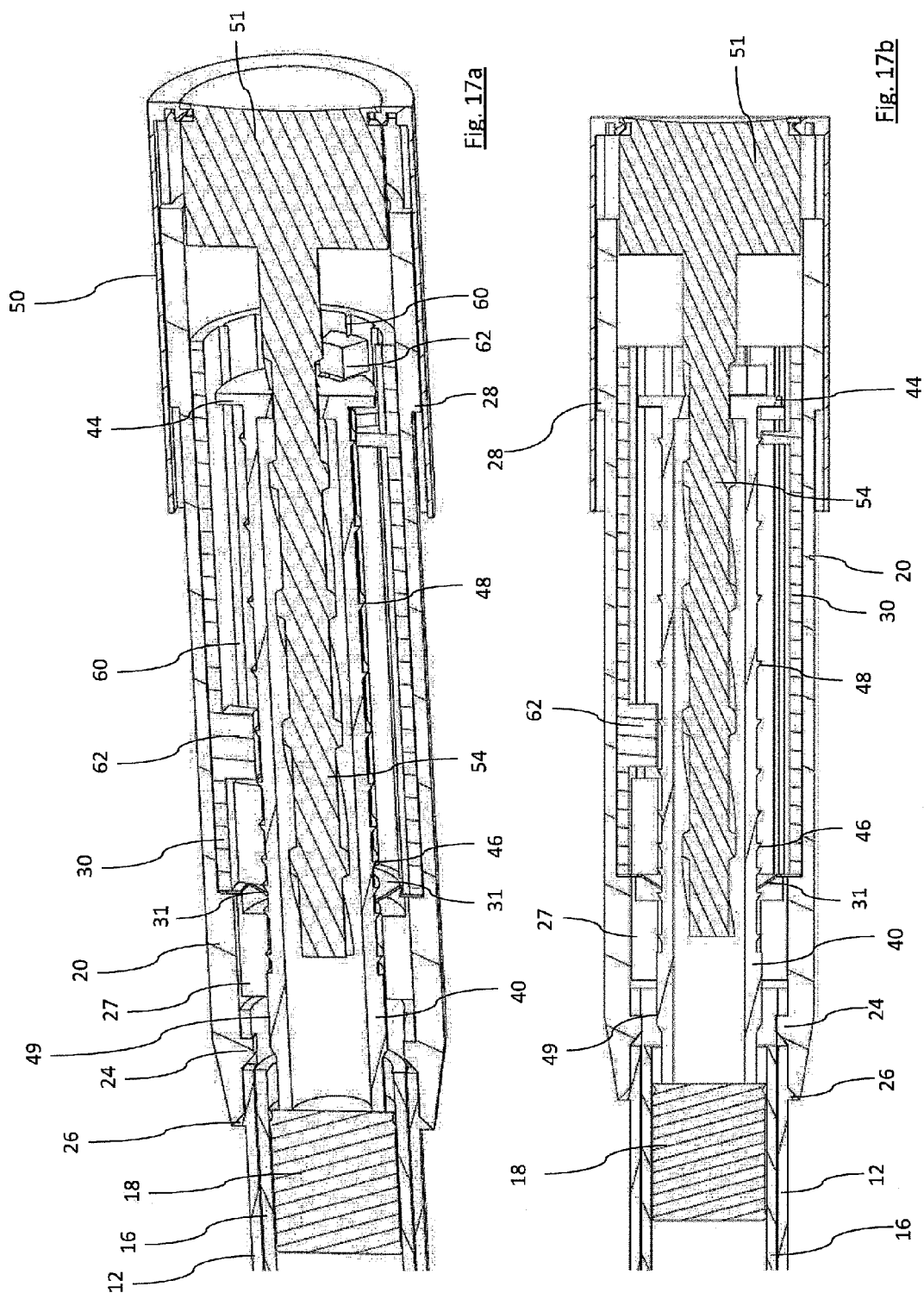

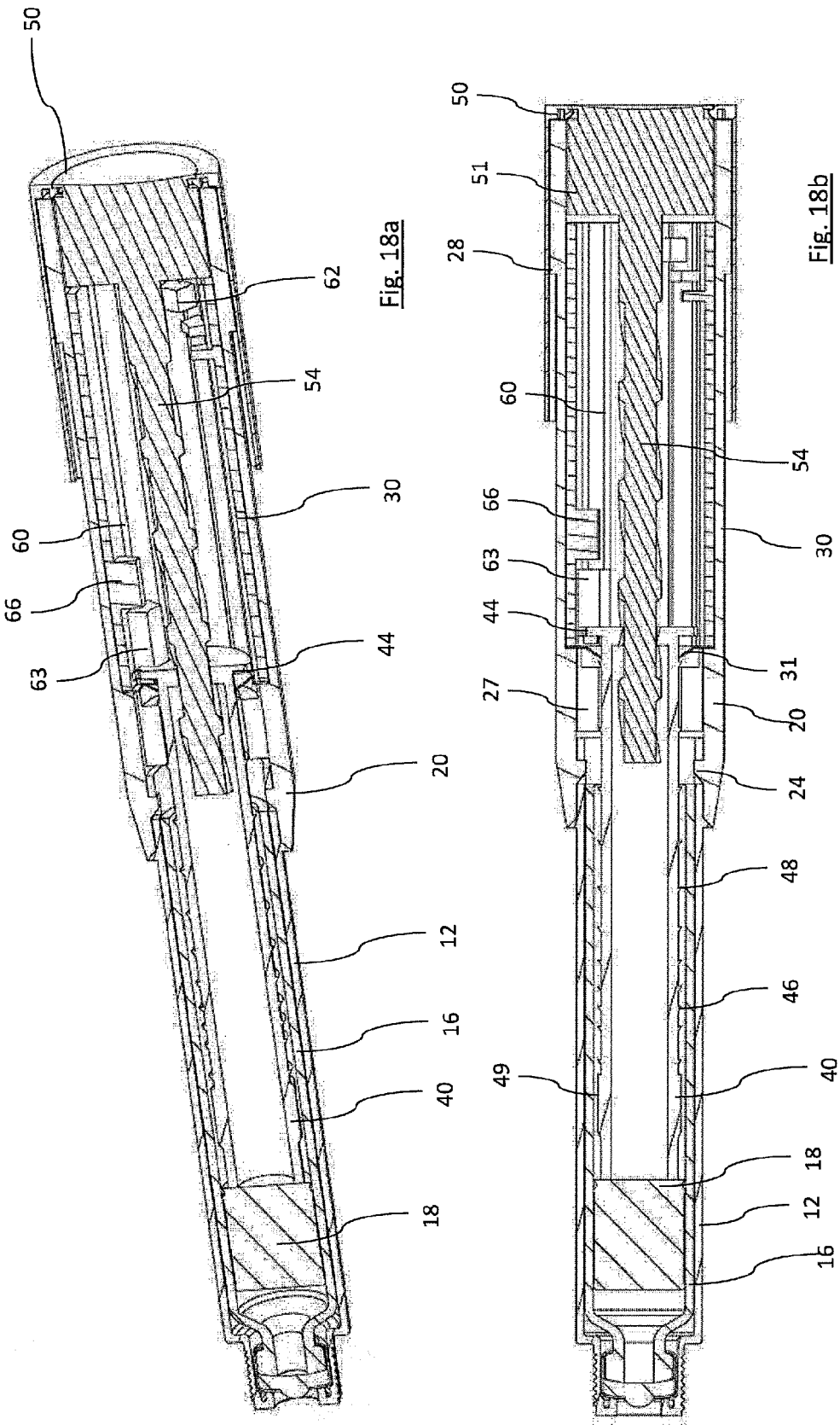

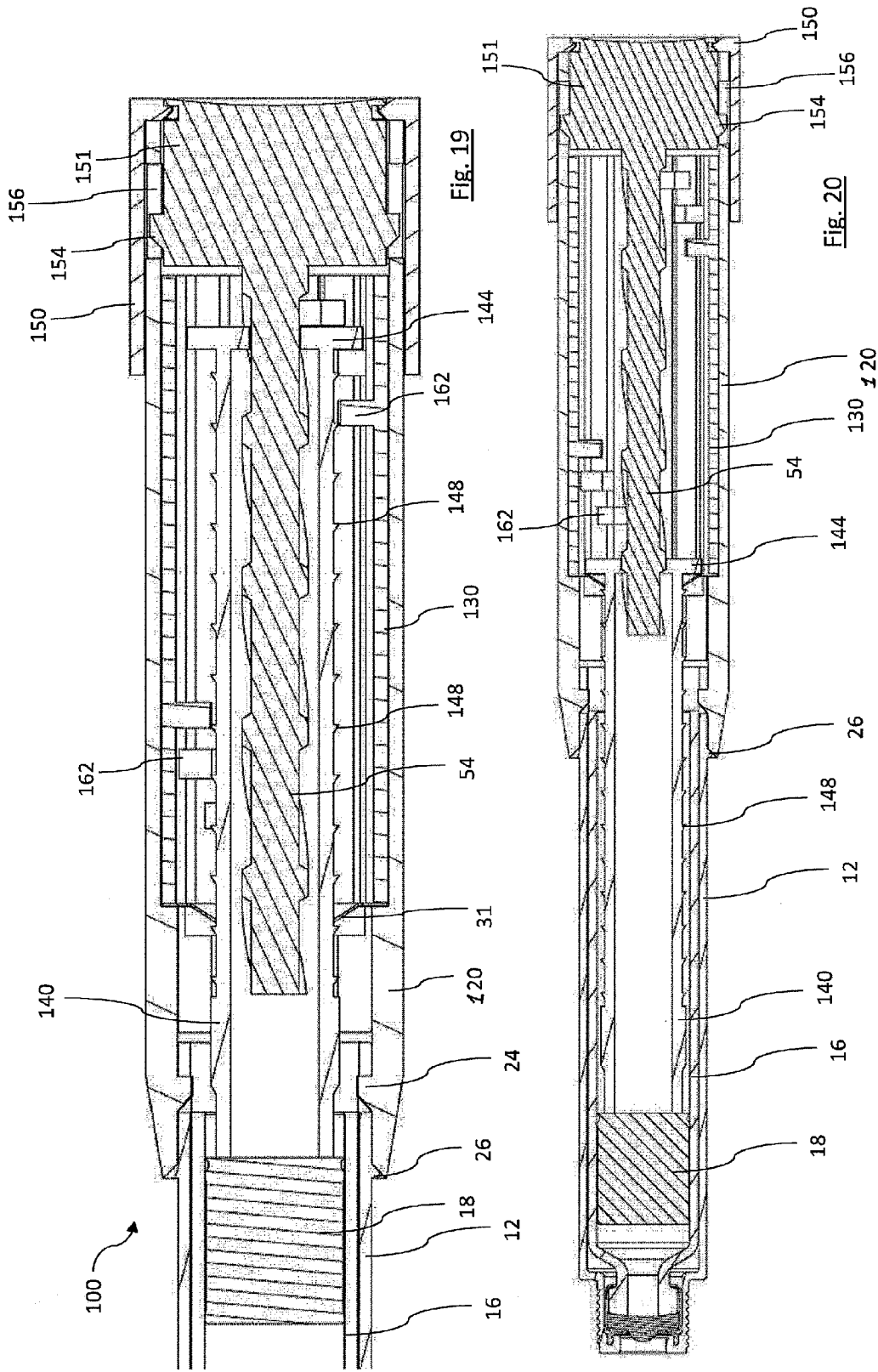

DRUG DELIVERY DEVICE

CROSS REFERENCE TO RELATED APPLICATIONS

The present application is a U.S. National Phase Application pursuant to 35 U.S.C. §371 of International Application No. PCT/EP2010/059542 filed Jul. 5, 2010, which claims priority to European Patent Application No. 09009132.3 filed on Jul. 14, 2009. The entire disclosure contents of these applications are herewith incorporated by reference into the present application.

FIELD OF INVENTION

The present invention relates to a drug delivery device, such as pen-type injectors, wherein a single or a number of pre-set doses of a medicinal product can be administered. The invention is particularly related to drug delivery devices being adapted to dispense a single or multiple controlled doses from a container.

BACKGROUND

User operated drug delivery devices are as such known in the prior art. They are typically applicable in circumstances, in which persons without formal medical training, i.e. patients, need to administer an accurate and predefined dose of a medicinal product, such as heparin or insulin. In particular, such devices have application, where medicinal product is administered on a regular or irregular basis over a short term or long-term period.

In order to accommodate with these demands, such devices have to fulfil a number of requirements. First of all, the device must be robust in construction, yet easy to use in terms of handling and in understanding by the user of its operation and the delivery of the required dose or medicament. The dose setting must be easy and unambiguous. Where the device is to be disposable rather than reusable, the device should be inexpensive to manufacture and easy to dispose (preferably being suitable for recycling). To meet these requirements, the number of parts required to assemble the device and the number of material types the device is made from need to be kept to a minimum.

Document U.S. Pat. No. 7,396,347 B2 discloses for instance an injector device for a syringe container with a piston rod arrangement operable to displace a moveable wall of the container in forward direction.

SUMMARY

It is therefore an object of the present invention, to provide an improved or alternative drug delivery device for dispensing of a dose of a medicinal product. The device should preferably be particularly easy and intuitive in handling, allow for an accurate dosing, comprise a simple internal structure, be inexpensive to produce and/or fast and easy to assemble. It is further preferable to provide a drug delivery device for dispensing numerous pre-defined doses of a medicinal product. The device should preferably comprise a reduced number of mechanical parts to be assembled. Moreover, the drug delivery device should expediently be mechanically stable and robust.

The present invention provides a drug delivery device for dispensing of a dose of a medicinal product. The device comprises a housing. The housing may have a proximal end and a distal end. The device comprises a container. The container may be disposed in the housing. The container comprises the medicinal product to be administered. A piston is retained within the container. The piston is preferably movably retained in the container. Depending on the purpose of the drug delivery device, a distal outlet of the container may be engaged with a needle, a cannula, an infusion tube or similar delivery devices. The container itself may be designed as replaceable or disposable ampoule, cartridge, carpule or syringe. The piston is displaceable in distal direction, in particular in distal direction with respect to the housing, preferably in order to expel a pre-defined dose of medicinal product from the container.

The drug delivery device further comprises a push-pull element. The push-pull element may be slideably disposed about the proximal end of the housing. The push-pull element, which may be adapted to be pushed and pulled by a user, is displaceable in proximal direction, in particular with respect to the housing, for setting or selecting of a dose. The push-pull element may be secured against rotational movement with respect to the housing. After setting of a dose and after a displacement of the push-pull element in proximal direction, the push-pull element is expediently displaceable in distal direction for dispensing of a dose.

The drug delivery device further comprises a piston rod having a distal end, which is adapted to interact with the piston. In particular, with its distal end, the piston rod may abut against the piston in order to transfer an axial displacement of the piston rod to the piston. The piston rod is further coupled with the housing and with the push-pull element.

The drug delivery device is further provided with coupling elements for converting a proximal displacement of the push-pull element into a rotational movement of the piston rod. Additionally, the coupling elements are adapted to convert a distal displacement of the push-pull element into an axial movement of the piston rod with respect to the housing, preferably in distal direction.

In this way, the push-pull element provides both, a dose setting as well as a dose dispensing in an easy, intuitive and unambiguous way. By pulling the push-pull element in proximal direction, a dose, in particular a pre-defined dose, may be set or selected. Subsequently, the respective dose can be dispensed and administered simply by pushing the push-pull element in the opposite, e.g. distal, direction.

Irrespective of a predetermined dose setting or dose selecting profile, the procedure for setting and/or dispensing of a dose is simplified and provides excellent reliability. The user is provided with a dose dispensing mechanism, which is easy in handling and which provides intuitive dose setting and dose dispensing. The general handling of the device is simplified, since dose setting may be achieved by pulling the push-pull element and dose dispensing may be conducted by pushing the push-pull element.

According to a first embodiment, the coupling elements comprise an axially extending screw and an inner thread of the piston rod, being threadedly engaged with the screw. Since the screw is rigidly coupled with the push-pull element, the piston rod and the push-pull element are also threadedly engaged. The axially extending screw of the push-pull element and the piston rod's inner thread are designed for a non-self-locking threaded engagement, such that, for instance, an axial and non-rotative movement of the push-pull element leads to a rotational movement of the piston rod. In this way, an axial movement of the push-pull element can either be transferred to an exclusive rotational movement, to an exclusive axial movement or to a combined rotational and axial movement of the piston rod.

According to a further embodiment, the piston rod is rotationally locked and moves axially in distal direction with respect to the housing during a displacement of the push-pull element in distal direction. Additionally or alternatively, the piston rod is axially locked and rotates with respect to the housing during a displacement of the push-pull element in proximal direction. Typically, in an initial state or after dispensing of a dose, the push-pull element rests at the proximal end of the housing. In order to set or to select a predetermined dose, the push-pull element can be pulled in proximal direction until it reaches a stop position. During this axial movement in proximal direction, the piston remains axially fixed and due to its threaded engagement with the push-pull element, it rotates about its longitudinal axis by a given angle.

By this rotation and preferably when reaching a stop position, the piston rod becomes released in axial direction as well as rotationally locked. Due to the coupling between the push-pull element and the piston rod and due to the restricted guidance of the piston rod, an axial displacement of the push-pull element in distal direction can be directly transferred to the piston rod and hence to the piston for dispensing of a predetermined dose. As soon as the push-pull element has again reached its initial, hence distal position, the piston rod may become again rotationally released and axially locked for a subsequent dose setting procedure.

Typically, the piston rod is either axially locked or rotatably locked with respect to the housing. A respective switching is typically initiated at the end of a dose setting procedure or at the end of a dose dispensing action.

According to a further preferred embodiment, the coupling elements comprise a recess and at least one guide and stop element. Typically, the dimension and geometry of the recess and the at least one guide and stop element mutually match. The recess is for instance adapted to receive the at least one guide and stop element.

Recess and guide and stop element are arranged at the piston rod and at an inner surface of the device, for example an inner surface of the housing. In a particular embodiment, the guide and stop element, which is typically disposed at the inner surface, may provide a double function. On the one hand it serves as a stop element in order to delimit an axial, in particular distal movement of the piston rod. On the other hand, if guide and stop element and the respective recess are in an aligned arrangement, the guide and stop element will allow for a pre-determined axial displacement of the piston rod with respect to the housing, but at the same time, it will impede a rotational movement of the piston rod.

Preferably, the piston rod comprises a radially outwardly extending flange comprising the recess, the recess being matched with the at least one radially inwardly protruding guide and stop element, the latter of which being preferably disposed at the inner surface of the housing. The outwardly extending flange of the piston rod is preferably arranged at the piston rod's proximal end. Its recess and the radially inwardly protruding guide and stop element of the housing provide a kind of key-lock mechanism, such that the piston rod's flange and the entire piston rod can be displaced in distal direction in a stepwise manner.

By means of an appropriate rotational movement of the piston rod with respect to the housing, the piston rod's recess can be brought in axial alignment with the guide and stop element. Since the recess and the guide and stop element have mutually corresponding external contours, the piston rod can be advanced or driven in distal direction, during which displacement the piston rod's recess passes along this particular guide and stop element. During such a passing along, a further rotational movement of the piston rod with respect to the housing is prevented by the engagement of the piston rods' recess and the at least one guide and stop element.

In typical embodiments, the coupling elements comprise numerous guide and stop elements, being disposed at an axial distance with respect to each other. These numerous guide and stop elements are typically staggeredly aligned in axial direction. In this way, the piston rod with its radially extending flange may pass along a first guide and stop element being axially aligned with the flange's recess. If a neighbouring guide and stop element is not co-aligned with this first guide and stop element, this second guide and stop element will serve as a stopper for delimiting an axial displacement of the piston rod, since a residual portion of the piston rod's flange will abut against this second guide and stop element.

According to another preferred embodiment of the invention, the at least one radially inwardly protruding guide and stop element is disposed at the inner surface of a guiding sleeve fixed in the housing of the drug delivery device. The guiding sleeve preferably comprises numerous guide and stop elements being arranged in a predefined pattern at the sleeve's inner surface. In terms of a key-lock mechanism, the guiding sleeve serves as a lock, whereas the piston rod with its flange and recess corresponds to a key being axially moveable in distal direction if aligned and rotated appropriately.

In preferable embodiments, the pattern of the guide and stop elements governs the sequence and the size of the predetermined doses. In this way, the design and embodiment of a guiding sleeve is decisive, e.g. on the number and the size of doses to be administered by the device. By making use of different types of guiding sleeves and corresponding piston rods, for example each providing a specific and different mechanical code, the drug delivery device can be provided in various different configurations, simply by interchanging the guiding sleeve and piston rod.

In case, that the drug delivery device is designed as disposable pen-type injector, a complete set of different configurations can be provided, simply by making use of the appropriate guiding sleeve, whereas all other components, in particular the housing and the push-pull element, may remain substantially unaltered.

According to another preferred embodiment of the invention, the inner surface of the guiding sleeve or the inner surface of the housing comprises a number of helically arranged radially inwardly protruding guide and stop elements. In particular, neighbouring guide and stop elements are disposed at a given axial distance. Furthermore, neighbouring guide and stop elements are disposed at an angular offset with respect to the inner circumference of the guiding sleeve. In this way, each guide and stop element allows for a distinct axial displacement of the piston rod as soon as the piston rod's recess matches with the respective guide and stop element. This axial movement is then delimited by a subsequent guide and stop element interacting with the piston rod's flange.

During a subsequent dose setting procedure, the piston rod rotates about a predetermined angle until the flange's recess is again aligned with the subsequent guide and stop element. As soon as such an alignment is reached, also this subsequent guide and stop element allows for another axial displacement of the piston rod and hence for another dispensing of a predetermined dose.

According to a further embodiment, the axial size and/or the axial distance of consecutively arranged guide and stop elements determines the size of the respective doses. The axial dimension of the guide and stops elements and their axial distance determine and govern the step size of the stepwise axial movement of the piston rod in proximal direction.

Depending on size, distance and/or arrangement of the various guide and stop elements, a predetermined administering profile for the medicinal product can be provided. If for instance, any dose to be dispensed should be equal in size, the axial size of merely all guide and stop elements is substantially equal. Additionally, they are arranged equidistant in axial direction.

In another scenario, where multiple controlled ejections of different sizes are required, the size, angular arrangement and axial distance of the guide and stop elements may vary accordingly. It is for instance conceivable, that the dose size should increase with each dispensed dose. This requirement can be fulfilled for instance with a guiding sleeve having numerous guide and stop elements disposed at increasing axial distance in distal direction. By varying axial size, angular arrangement and/or axial distance of the various guide and stop elements, multiple controlled ejections, each of which with doses of different size can be administered in a well-defined way.

According to another preferred embodiment, consecutive guide and stop elements are spaced at an axial distance, which is equal to or exceeding the axial size of the piston rod's flange. This is to provide a rotational disengagement between piston rod and guide and stop element at the end of a dose dispensing step, when the piston rod's flange abuts against a consecutive guide and stop element. As soon as such an abutment configuration is reached, the piston rod's flange has completely passed along the preceding guide and stop element. Therefore, the flange's recess is no longer engaged with the preceding guide and stop element and the entire piston rod is free to rotate for a certain angle until the recess is aligned with the consecutive guide and stop element.

In a further preferred embodiment, the piston rod's flange adjacent to its recess comprises a stopper, which extends axially in distal direction and which is adapted to abut against a guide and stop element for delimiting a rotation of the piston rod. This stopper is preferably intended to delimit the rotational movement of the piston rod during a dose setting action, initiated by pulling the push-pull element in proximal direction.

The axial dimensions of the piston rod's flange and the stopper together exceed the axial distance between consecutive guide and stop elements. By means of the stopper, the rotational movement of the piston rod is delimited at an angular position, in which the flange's recess is aligned with the respective guide and stop element. Preferably, an abutment surface of the stopper aligns with a boundary of the flange's recess.

According to another preferred embodiment of the invention, the piston rod comprises a plurality of annular retaining elements on its external circumference. These annular retaining elements are axially spaced with respect to each other. They are further adapted to keep the piston rod at a given axial position, in particular during a dose setting procedure, when the push-pull element is subject to a displacement in proximal direction. The axial distance or spacing between the annular retaining elements is typically governed by the pattern, size and distance of the guide and stop elements of the housing or the respective guiding sleeve. Therefore, depending on the pattern of guide and stop elements, also the annular retaining elements of the piston rod may be equidistantly spaced or the axial distance between consecutive annular retaining elements may vary according to the size and distance of the guide and stop element's pattern.

In a further embodiment, the retaining elements are designed as circumferential protrusion and/or as circumferential recess. They may comprise circumferential notches or grooves or they may comprise respective annular projections or lugs. Preferably, in an axial cross-section, the retaining elements comprise a kind of saw-tooth profile. In this way, the retaining element can provide a unidirectional axial motion of the piston rod relative to the housing. In detail, the saw-tooth profile supports an axial movement of the piston rod in distal direction and serves to prevent and to impede an opposite movement of the piston rod in proximal direction. By means of the retaining elements, a kind of ratchet function can be provided.

In still another embodiment, the piston rod's flange and the inner surface of the housing or the inner surface of the respective guiding sleeve comprise mutually corresponding axial guiding means. Additional to the guiding function of the flange's recess and the various guide and stop elements, these axial guiding means provide an additional guiding function in axial direction. Furthermore, the axial guiding means of the piston rod's flange and the inner surface of either housing or guiding sleeve may provide or enhance a rotational locking of the piston rod relative to the housing, in particular during a dose dispensing procedure. Moreover, the axial guiding means are further adapted to allow for a unidirectional rotation of the piston rod during dose setting and to impede and to prevent an opposite rotational movement during dose dispensing. In particular, at the end of a dose dispensing procedure, when the piston rod's flange is positioned in the gap between neighbouring guide and stop elements, said axial guiding means allow for a rotation of the piston rod in response to a pull movement of the push-pull element.

During this dose setting, the axial guiding means can be temporally disengaged until the piston rod has been rotated by a predetermined angle. As soon as the piston rod reaches a stop position, in particular an angular stop position, the axial guiding means may engage again in order to prevent an opposite rotational movement of the piston rod, in particular at the beginning of a subsequent dose dispensing.

In a further preferred embodiment, these guiding means comprise a plurality of radially inwardly protruding and axially extending projections on the inner surface of the housing or on the respective inner surface of the guiding sleeve. Furthermore, the guiding means comprise at least one prong on the piston rod's flange. This prong is adapted to interlock with the radially inwardly protruding projections for axially guiding the piston rod with respect to the housing. Preferably, the prong is resilient. Typically, if several resilient prongs are provided, they will be arranged at the flange's circumference in regular order. If for instance two resilient prongs are provided, they are preferably arranged at opposite sides of the piston rod's flange, i.e. at a relative angle of 180°.

The inwardly protruding and axially extending projections may have a symmetric or asymmetric shape. Preferably, they may comprise a saw-tooth profile. In interaction with corresponding prongs on the piston rod's flange, the axial guiding means provide a unidirectional rotation of the piston rod in the housing or in the respective guiding sleeve, while a rotation in opposite direction is inhibited. The radial dimension of the inwardly protruding projections of the axial guiding means is typically much smaller than the radial dimensions of the radially inwardly protruding guide and stop elements. Furthermore, each radially inwardly protruding projection may be intersected by at least guide and stop element. Also, the number of guide and stop elements at least equals the number of radially inwardly protruding projections.

The dimensions and the arrangement of the radially inwardly protruding projections, the guide and stop elements as well as geometry and size of the piston rod's flange, its recess and the annular retaining elements are mutually adjusted. In this way, a prong of the piston rod's flange may interlock with the radially inwardly protruding projection of the housing just when a rotational movement of the piston rod is delimited by the piston rod's stopper abutting against a guide and stop element.

Additionally, the resilient prong and the axially extending projections of the housing or the respective guiding sleeve are expediently adapted to generate an audible feedback, such like a clicking noise, indicating to the user, that the piston rod has reached a predefined stop position, from which a dose dispensing action can be conducted.

According to another preferred embodiment, the drug delivery device further comprises a locking element disposed in the housing and being further adapted to inhibit a displacement of the piston rod in proximal direction. This locking element is particularly adapted to interact with the annular retaining elements of the piston rod. It may be designed as a metal component. The locking element may be disposed in the housing, e.g. near the furthermost distally arranged guide and stop element. Instead of a separate component, this locking element may also be integrally designed as a portion of the housing or of the respective guiding sleeve. It may be disposed near the guiding sleeve's distal end in the housing.

Additionally, in a further embodiment, this locking element is of disk-like or ring-like shape and comprises at least one radially inwardly protruding projection, which is adapted to interact with a corresponding retaining element disposed at the circumference of the piston rod. The locking element may be further adapted to surround the piston rod. The locking element together with the annular retaining elements of the piston rod is preferably adapted to allow for an axial displacement of the piston rod in distal direction but to prevent an opposite movement in proximal direction.

The arrangement and design of the retaining elements, the locking element as well as the pattern of guide and stop elements is such that the locking element and the annular retaining elements of the piston rod mutually engage as soon as a dose dispensing step is terminated by the piston rod's flange abutting against a subsequent guide and stop element. Also here, the engagement of locking element and annular retaining element may generate an audible clicking noise indicating, that the device is ready for a subsequent dose setting procedure, in which the piston rod is free to rotate but kept at its axial position by means of the interacting locking element and the annular retaining elements of the piston rod.

It will be apparent to those skilled in the art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE FIGURES

Without any limitation, the present invention will be explained in greater detail below in connection with preferred embodiments and with reference to the drawings in which:

FIG. 4 shows in another perspective and semitransparent illustration the guiding sleeve with helically arranged guide and stop elements, FIG. 5 shows the piston rod in a perspective illustration, FIG. 10 depicts a locking element, FIG. 11 shows the locking element according to FIG. 10 in a perspective side view;

FIG. 17a depicts a perspective cross-sectional view of the drug delivery device after a first dose dispensing, FIG. 17b shows the configuration of FIG. 17a in longitudinal cross section, FIG. 18a shows the drug delivery device after the last dose has been dispensed, FIG. 18b shows the configuration of FIG. 18a, in longitudinal cross section, FIG. 19 shows another, simplified embodiment of the drug delivery device after a first dose dispensing, FIG. 20 shows the embodiment of FIG. 19 after the last dose has been dispensed.

DETAILED DESCRIPTION

Figure 1:
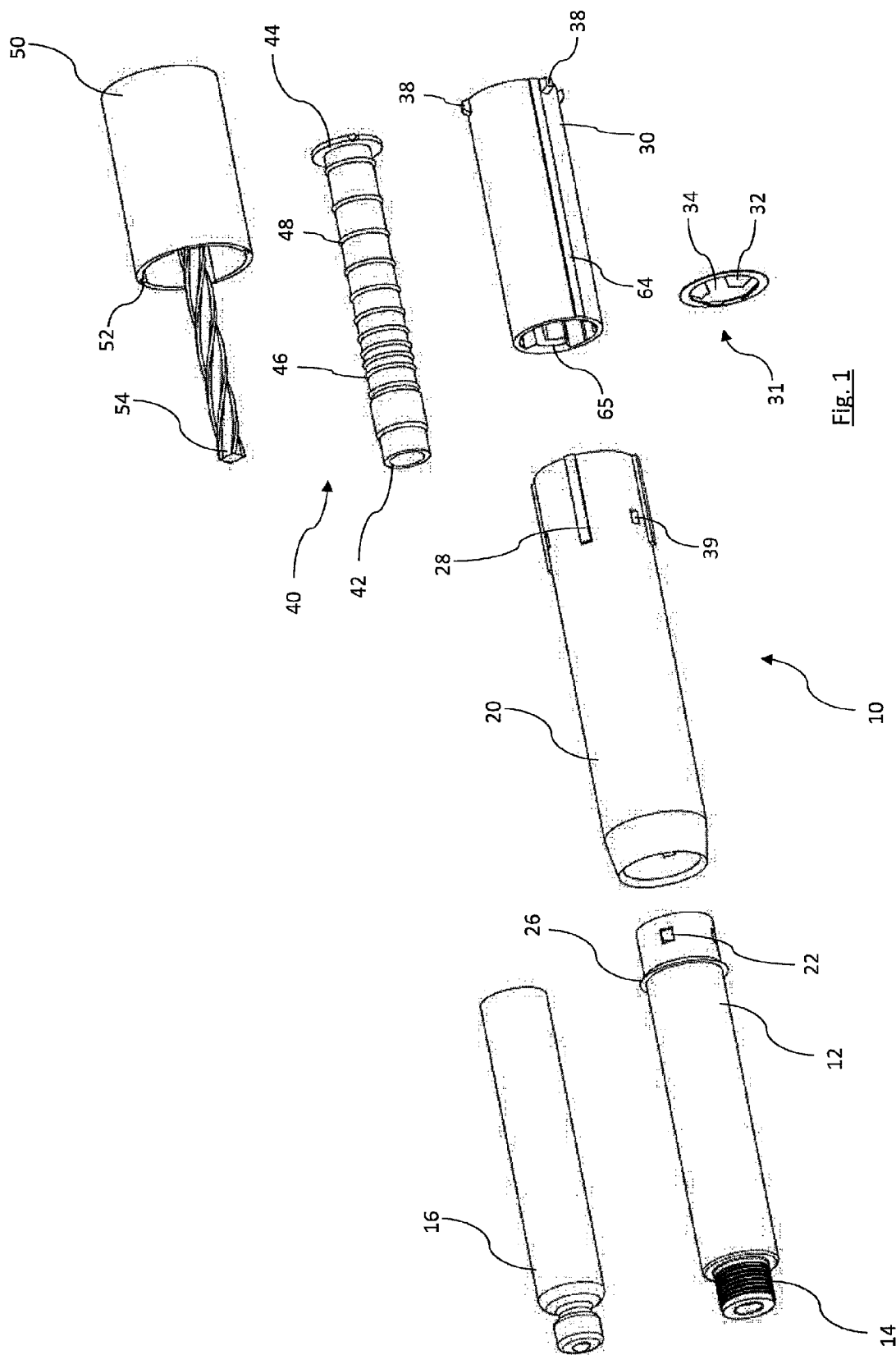
FIG. 1 schematically illustrates the various components of the drug delivery device in an exploded view.

A first embodiment of the drug delivery device 10 of pen-injector type is illustrated in an exploded view in FIG. 1. The drug delivery device 10 comprises a housing having a proximal component 20 and a distal component 12. Both components 12, 20 have a sleeve-like cylindrical geometry. The distal component 12 is adapted to house a container 16 comprising a medicinal product to be dispensed. The container 16 may be designed as ampoule, as carpule, cartridge or other syringe-like container. The distal housing component therefore serves as a cartridge holder.

At its distal end the housing or cartridge holder 12 has a socket 14, which is designed as a stepped down neck portion and which provides at an inside abutment for a corresponding socket portion of the container 16. At its outside, the stepped down socket 14 comprises a thread serving as a mount for an injection needle, a cannula or the like.

At its proximal end, the container has a piston 18 (cf. FIGS. 17 and 18), which is to be stepwise pushed in distal direction by means of a piston rod 40, in order to eject and to dispense a well-defined dose of medicinal product.

As can further be seen from FIGS. 8, 9 and 17 and 18, the distal housing component 12 and proximal housing component 20 can mutually engage by means of a positive locking For this purpose, the distal housing component 12 comprises numerous recesses 22 at the outer circumference of its proximal end. Accordingly, the proximal housing component 20 at its distal inner surface comprises corresponding detent elements 24, adapted to fit into and to match with the recesses 22 of the distal housing component 12. Further, the distal housing component 12 comprises an annular collar 26, which serves as abutment for the distal end face of the proximal housing component 20.

The drug delivery device 10 is preferably designed as disposable device, wherein after a dispensing of the last dose, the entire device 10 is intended to be disposed. In this case the entire device 10 could be subject to a recycling process, in which the drive mechanism disposed in the proximal housing component 20 can be reused. Alternatively, e.g. by the positive locking of distal and proximal housing components 12, 20, the entire drug delivery device 10 could also be disassembled, e.g. for the purpose of replacing an empty container 16. Hence, the device could also be designed as reusable device.

Figure 2:
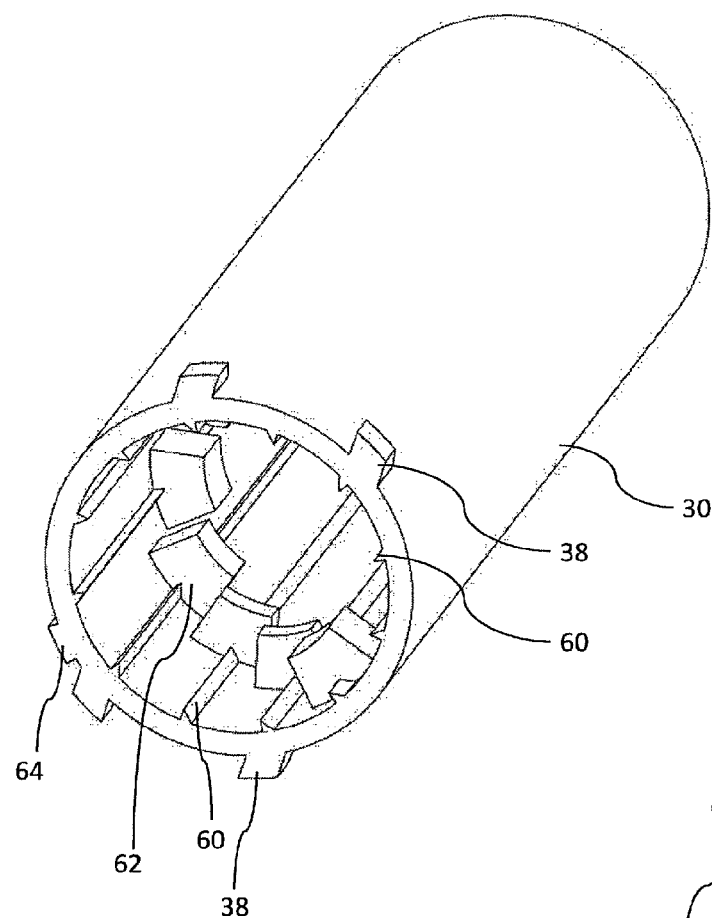
FIG. 2 shows a guiding sleeve in perspective illustration as seen from its proximal end.
Figure 3:
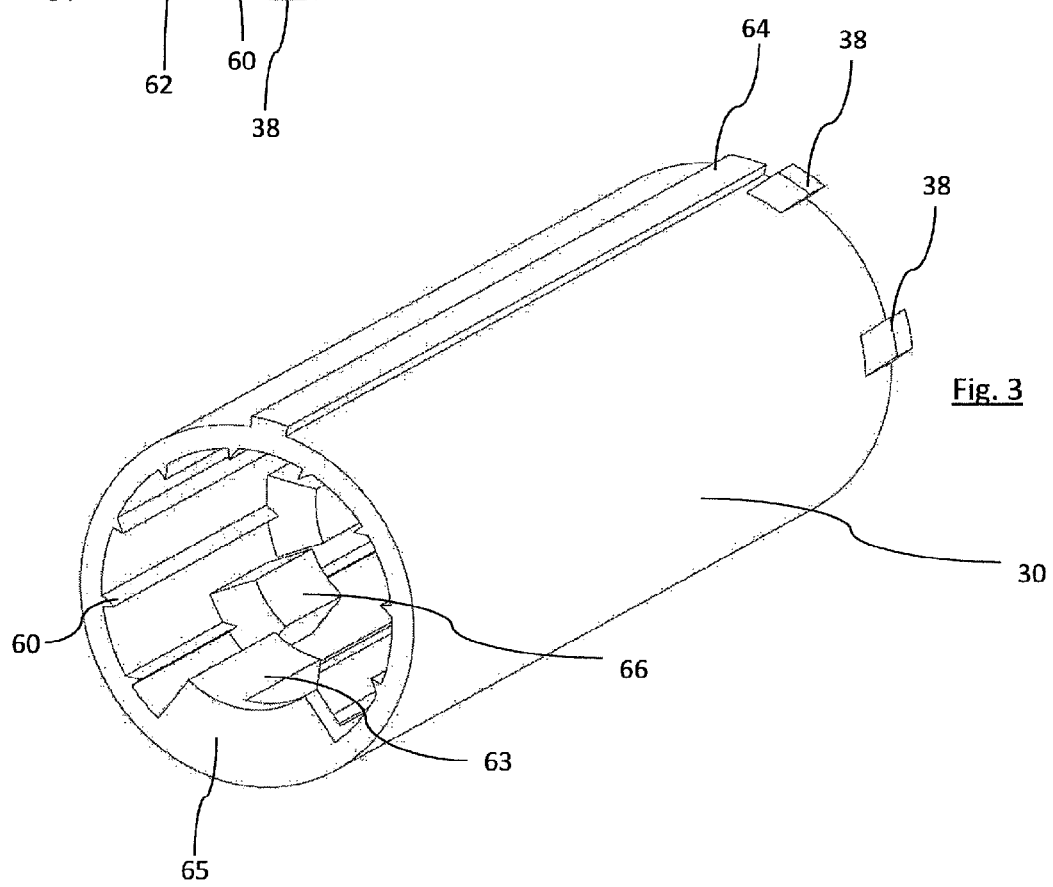
FIG. 3 shows the guiding sleeve according to FIG. 2 as seen from its distal end.
Figure 14A:
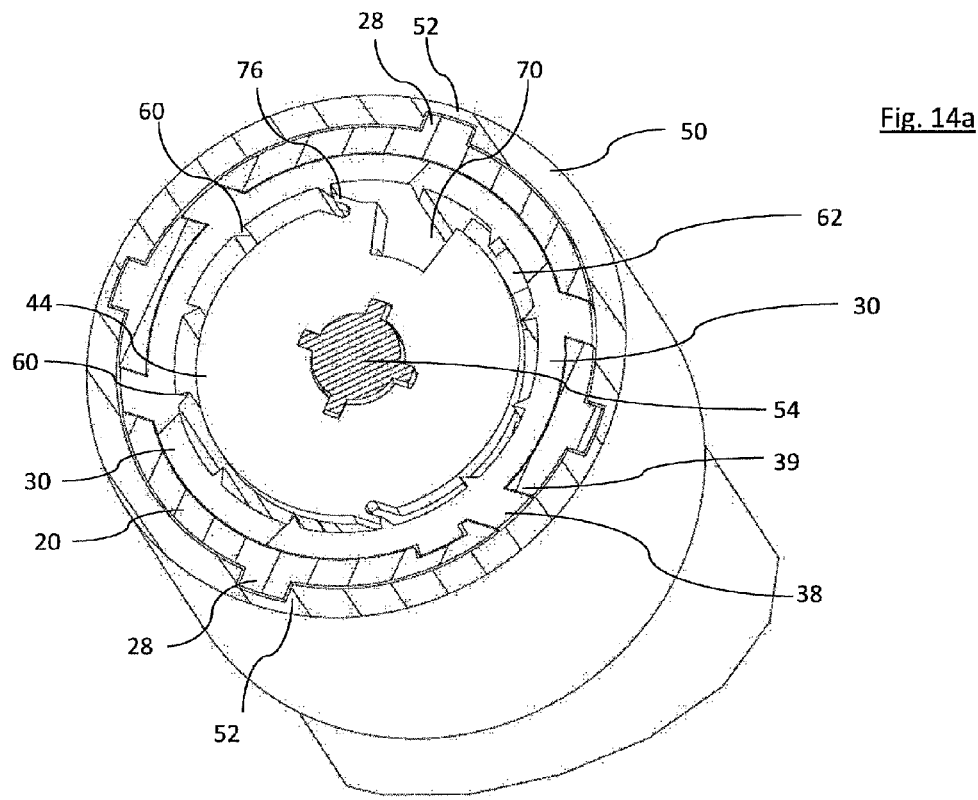
FIG. 14a shows a perspective cross-sectional illustration of the drug delivery device in a configuration prior to a dose setting procedure.
Figure 14B:
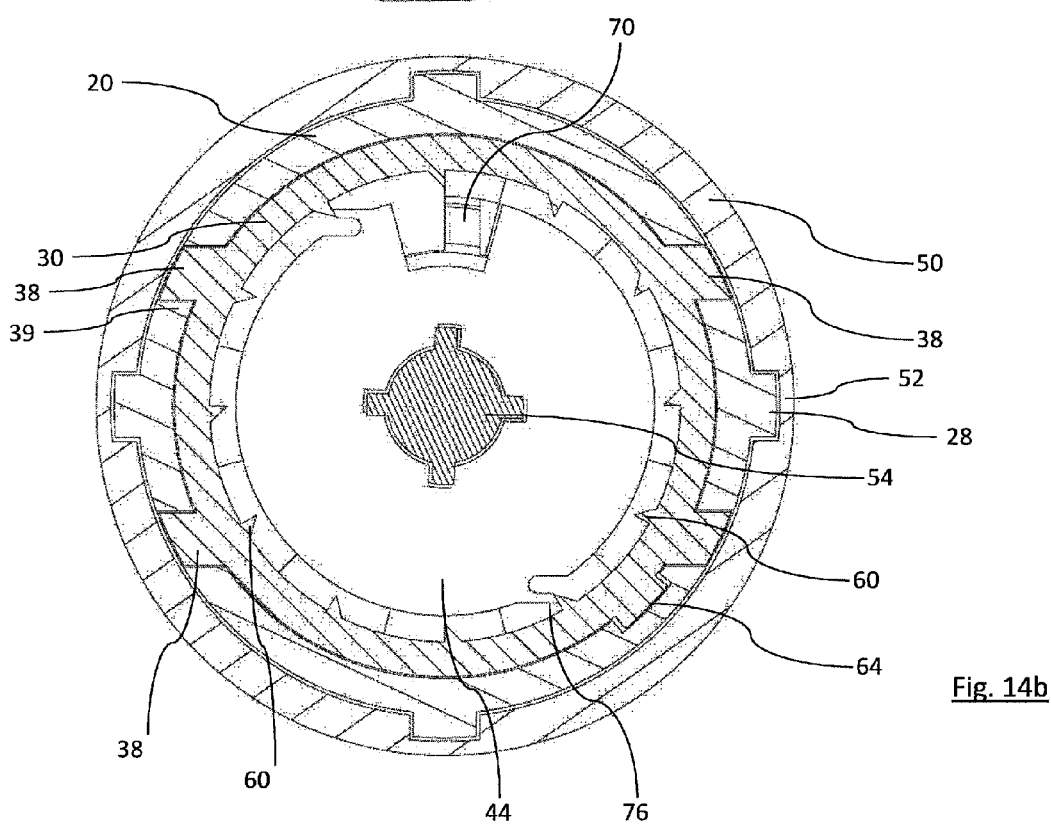
FIG. 14b shows the configuration of FIG. 14a in a transverse cross section.

The sleeve-like proximal housing component 20 is adapted to receive a guiding sleeve 30, which is shown in detail in FIGS. 2, 3 and 4. At its proximal end, the guiding sleeve 30 comprises various detent elements or protrusions 38, that fit into corresponding recesses 39 at the housing component's 20 proximal end, as can be seen in FIGS. 14, 15 and 16. Further, the guiding sleeve 30 comprises an axially extending protrusion 64 at its external surface. This protrusion 64 has the function of a symmetry breaking element and corresponds with a respective notch at the inner surface of the housing component 20. Due to this protrusion 64, the guiding sleeve 30 can be inserted into the proximal housing component 20 only in a well-defined orientation.

The guiding sleeve 30, as illustrated in FIGS. 2, 3 and 4 comprises various radially inwardly protruding guide and stop elements 62, 66 at its inner surface. The guide and stop elements 62, 66 have a somewhat rectangular or trapezoid-like shape. The guide and stop elements 62, 66 are arranged at different axial positions, wherein between neighbouring guide and stop elements 62, 66 an axial gap 68 is formed. Further, neighbouring guide and stop elements 62, 66 are arranged at a circumferential angular offset. In this way, the series of guide and stop elements 62, 66 describes a helix.

The piston rod 40 interacting with the piston 18 of the container 16 is guided in the guiding sleeve 30. This is shown in detail in FIGS. 5, 6 and 7. With its distal face 42, the piston rod 40 abuts against the piston 18, as it is illustrated in FIGS. 17 and 18, for example. At its opposite proximal end, the piston rod 40 comprises a radially outwardly extending flange 44. The diameter of the flange 44 corresponds to the inner diameter of the guiding sleeve 30. Further, the flange 44 comprises a recess 70, that matches with the transverse geometry of the various guide and stop elements 62, 66 of the guiding sleeve 30.

Since the gap 68 between axially neighbouring guide and stop elements 62, 66 slightly exceeds the axial size of the piston rod's flange 44, the piston rod 40 can be displaced axially in distal direction through the guiding sleeve 30 in a stepwise alternating axial and rotational movement. The guiding sleeve 30 with its defined pattern of guide and stop elements 62, 66 and the piston rod 40 with its flange 44 provide a kind of key-lock mechanism for the purpose of dispensing multiple controlled and well-defined doses from the container 16.

As soon as the recess 70 of the piston rod's flange 44 is properly aligned with a guide and stop element 62, 66, as it is, for instance, illustrated in FIG. 15, the piston rod 40 can be displaced in distal direction until the flange 44 abuts against a neighbouring guide and stop element, as for instance illustrated in FIG. 16. Having reached such a stop position, the flange 44 is typically disposed in a gap 68 between two neighbouring guide and stop elements 62, 66. In this way, the piston rod 40 can in principle be rotated by a given angle while it remains locked in axial direction. As soon as the flange's recess 70 is aligned with the next guide and stop element 62, 66 of the guiding sleeve 30, another dose dispensing can be conducted.

The guide and stop elements 62, 66 provide a multiple functionality. On the one hand the guide and stop elements 62, 66 together with the flange 44 of the piston rod 40 provide a stop for delimiting an axial movement of the piston rod 40 with respect to the guiding sleeve 30. On the other hand, during a dose dispensing step, in which the piston rod 40 is subject to a displacement in distal direction, the engagement of recess 70 and guide and stop element 62, 66 inhibits a rotational movement of the piston rod 40.

Figure 12:
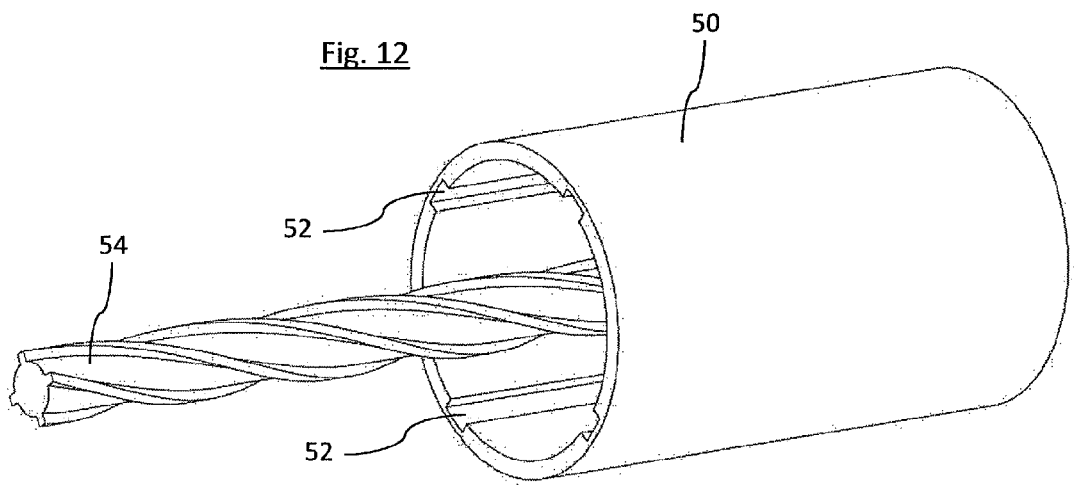
FIG. 12 shows the push-pull element with rigidly attached screw.
Figure 13:
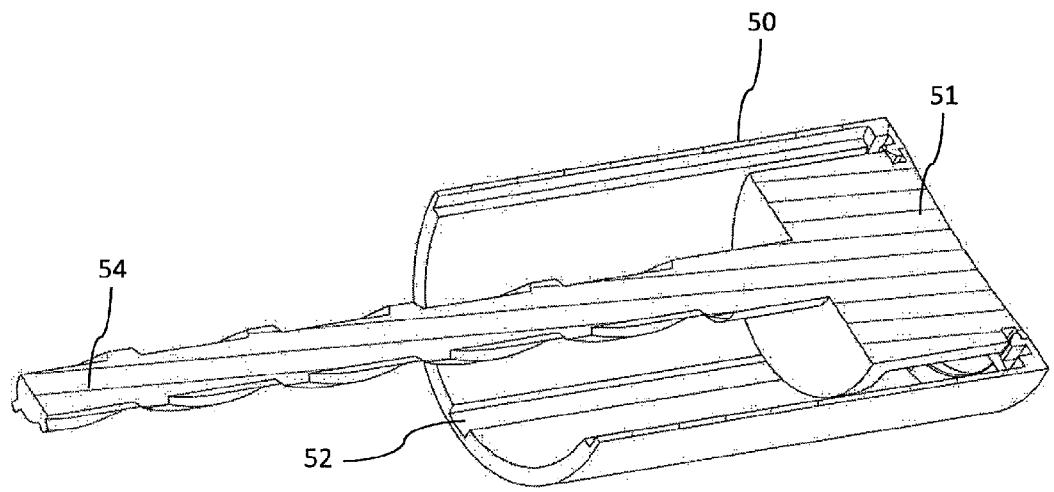
FIG. 13 shows the push-pull element according to FIG. 12 in a cross-sectional view.

Both alternate movements, namely translational and rotational movement of the piston rod 40 are conducted by means of the push-pull element 50, slidably arranged at the proximal end of the proximal housing component 20. The push-pull element 50 is rigidly coupled with a screw 54, as illustrated in FIGS. 12, 13, 17 and 18. The screw is integrally formed with a radially widened cylindrical portion 51, having a diameter matching with the inner diameter of the housing's proximal end. The screw 54 is threadedly engaged with an inner thread 72 of the piston rod 40. The push-pull element 50 is axially guided about the proximal end of the proximal housing component 20 by means of mutually corresponding ribs 28 and notches 52, as illustrated by the combination of FIGS. 9 and 12. In this way, a restricted axial guidance of the push-pull element 50 can be provided.

The screw 54 and the inner thread 72 are designed as non-self-locking threaded engagement. Consequently, by means of pulling the push-pull element 50 in proximal direction together with its rigidly attached screw 54, a rotational movement of the piston rod 40 for the purpose of setting a dose, can be initialized.

Furthermore, an opposite push movement of the push-pull element 50 in distal direction can be directly transferred in a respective axial displacement of the piston rod 40 in distal direction, for the purpose of dispensing a predefined dose.

The screw 54, the corresponding inner thread 72 of the piston rod 40 and the guide and stop elements 62, 66, serve as coupling elements for converting a proximal displacement of the push-pull element 50 into a rotational movement of the piston rod 40 and for converting a distal displacement of the push-pull element 50 into an axial movement of the piston rod 40 with respect to the housing 20 or the respective guiding sleeve 30.

In order to provide an exclusive rotational movement of the piston rod 40 during a dose setting procedure and to provide an exclusive axial movement of the piston rod 40 during a dose dispensing procedure, the drug delivery device 10 comprises various additional retaining and guiding means.

As can be further seen in FIGS. 2, 3, 4, 14, 15 and 16, the guiding sleeve 30 comprises various axially extending projections 60 on its inner surface, intersecting the guide and stop elements 62, 66 or interrupted by the guide and stop elements. The projections 60 are adapted to interact with at least one resilient prong 76 on the piston rod's flange. The prong 76 and the corresponding projections 60 are adapted to provide an additional axial guiding of the piston rod 40 during a dose dispending. Further, the resilient prong 76 on the outer circumference of the piston rod's 40 flange 44 serves to inhibit a rotational movement of the piston rod 40 in a direction opposite to a rotation required for setting a dose.

For this purpose, the axially extending projections 60 have a saw-tooth-like triangular shape. By comparison of the configuration illustrated in FIGS. 14, 15 and 16, the design of corresponding projections 60 and prong 76 is such that a clockwise rotational movement of the piston rod 40 is allowed, whereas a counter clockwise rotation is inhibited, since the prong 76 always abuts against a steep edge of the projection 60. Additionally, the interaction of resilient prong 76 and corresponding projection 60 generates an audible noise, thus indicating, that the device 10 is prepared for dispensing of a dose.

Additionally, the device 10 comprises a locking element 31, as illustrated in detail in FIGS. 10 and 11. The locking element 31, which is of disk- or ring-like shape is disposed in the housing component 20 as illustrated in FIGS. 17-20. It comprises a through hole 36 being adapted to receive the piston rod 40. The locking element 31 further has radially inwardly pointing protrusions or projections 32 having a circular segment structure. Between the projections there are gaps 34 allowing for the projections to be bent in axial direction.

In an initial configuration, the protrusions 32 slightly project in distal direction, as illustrated in FIG. 11. The projections 32 are further adapted to interact with corresponding circumferential projections 46, 48 on the outer surface of the piston rod 40. Preferably, these circumferential projections, which serve as annular retaining elements 46, 48 have a saw-tooth profile in axial direction with a rising edge towards the distal direction and with a steep edge towards the proximal direction.

The locking element 31 always allows for a rotational movement of the piston rod 40 relative to the housing 20 or its respective guiding sleeve 30. Furthermore, the locking element 31 allows for an axial displacement of the piston rod 40 in distal direction. The engagement of locking element 31 with the annular projections 46, 48 of the piston rod 40 is adapted to inhibit an axial movement of the piston rod 40 in proximal direction.

This axial locking is of particular importance at the beginning of a pull movement of the push-pull element 50, because otherwise, if the piston rod 40 would not be axially locked, it could move in proximal direction, thus separating from the piston 18. By means of the locking element 31 such proximal movement of the piston rod 40 can be prevented and a pull of the push-pull element 50 can be entirely transferred to a rotational movement of the piston rod 40.

Figure 7:
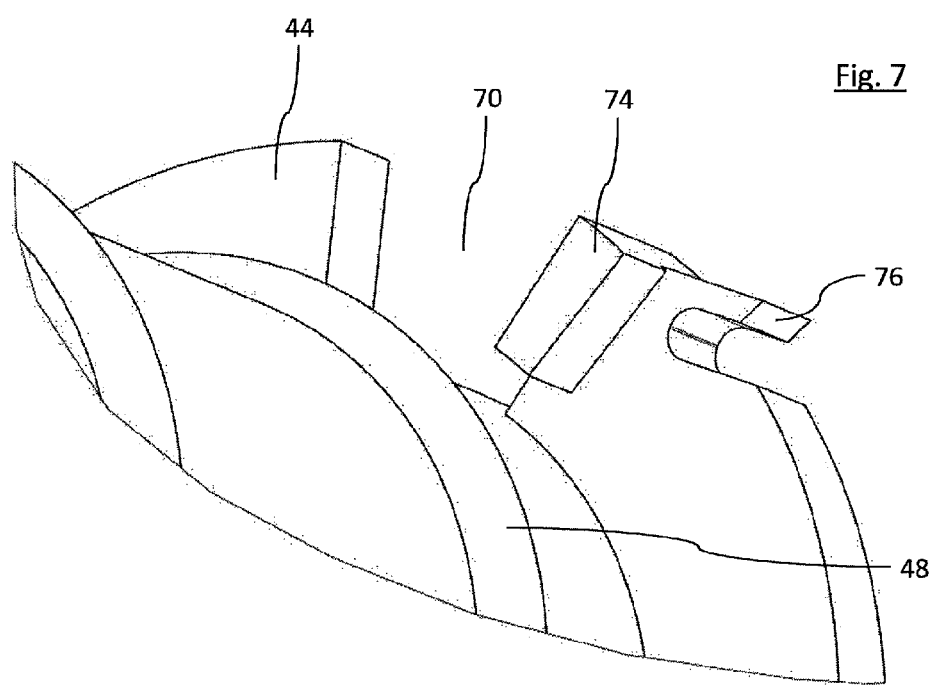
FIG. 7 shows the piston rod's flange with recess in an enlarged view, FIG. 8 schematically shows a distal part of the housing, FIG. 9 in a perspective view shows a proximal part of the housing.

In order to delimit a rotational movement, the piston rod 40 further comprises a stopper 74 on its flange 44 extending axially in distal direction, as shown in detail in FIG. 7. The stopper 74 is adapted to abut against a guide and stop element 62, 66 at the end of a dose setting procedure. Additionally, it is intended, that the prong 76 interacts with a respective axial projection 60, providing audible feedback, signalizing that the dose setting procedure has terminated and that a dose dispensing procedure can be started. Since the stopper, as illustrated in FIG. 7 is disposed adjacent the flange's recess 70, a proper alignment of guide and stop element 62, 66 and recess 70 is reached, as soon as the stopper 74 abuts against the respective guide and stop element 62, 66.

Figure 15A:
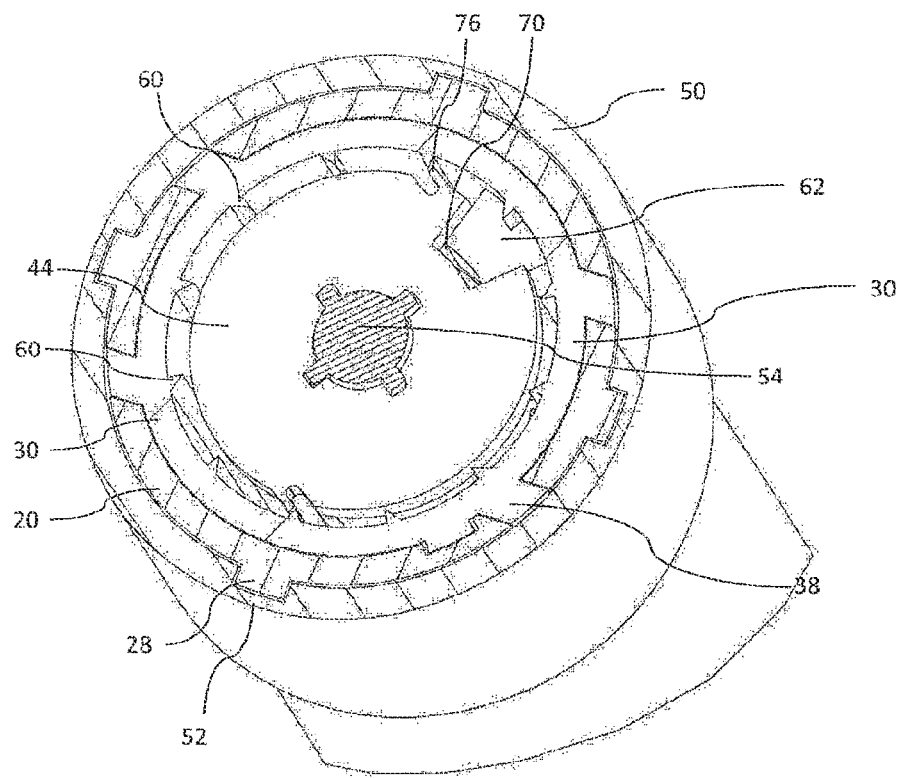
FIG. 15a shows the device according to FIG. 14 after a dose setting procedure.
Figure 15B:
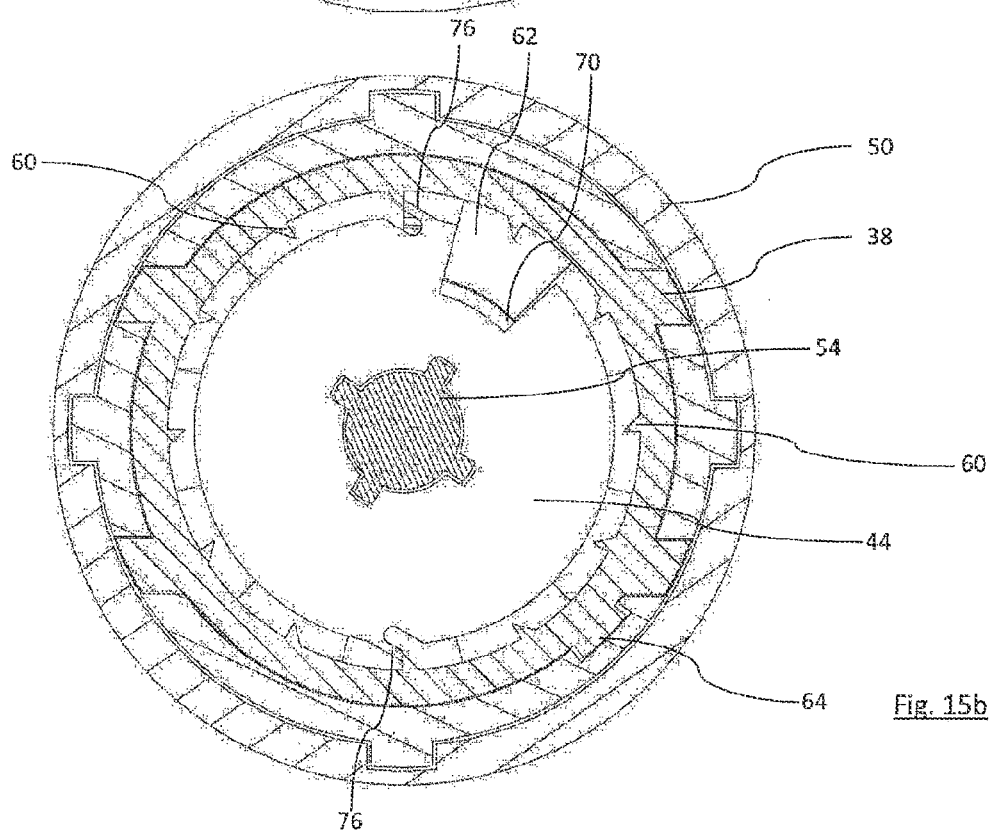
FIG. 15b shows the configuration of FIG. 15a in a transverse cross section.
Figure 16A:
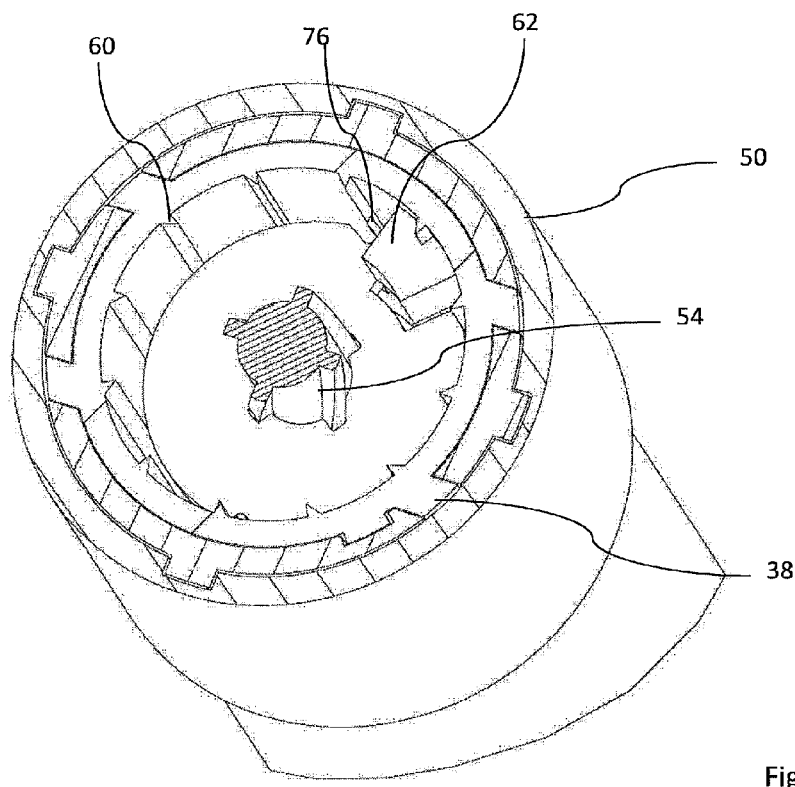
FIG. 16a illustrates the device according to FIGS. 14 and 15 during or after a dose dispensing procedure.
Figure 16B:
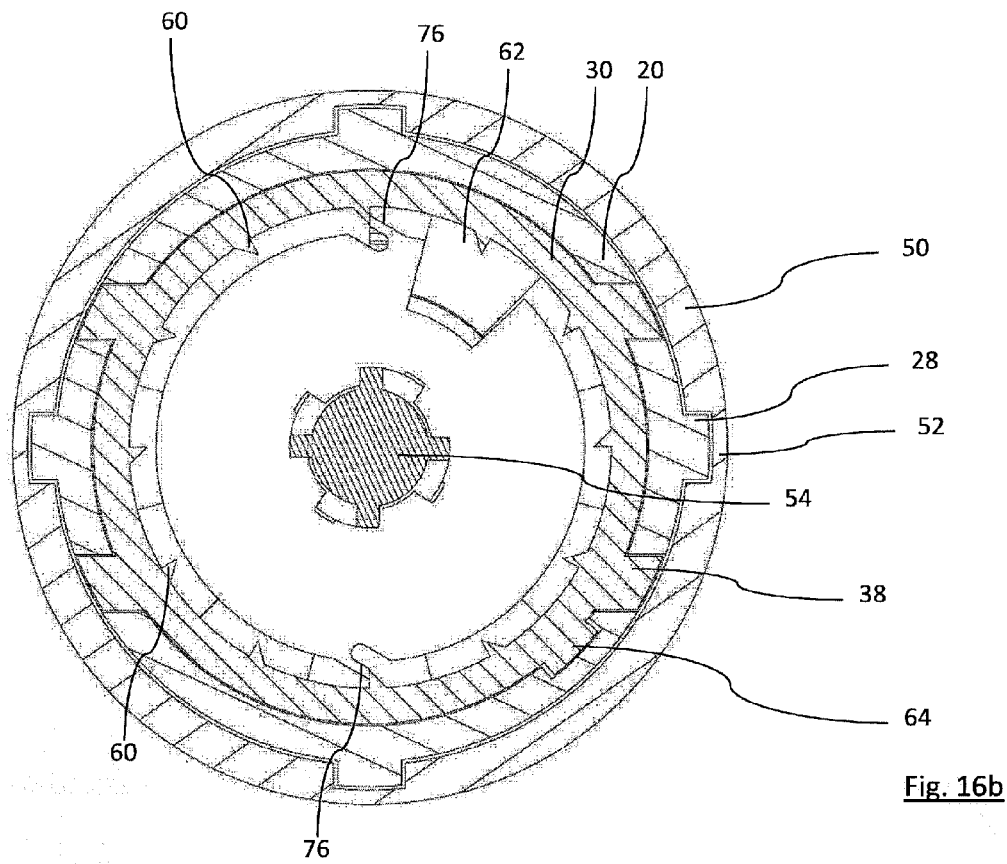
FIG. 16b shows the configuration of FIG. 16a in a transverse cross section.

The rotational movement of the piston rod 40 during dose setting is illustrated by a comparison of FIGS. 14 and 15. A configuration after or during a subsequent dose dispensing is illustrated in FIGS. 16a and 16b. Compared to FIGS. 15a and 15b, the piston rod 40 and its flange 44 have moved a predetermined distance in proximal direction, until the flange 44 abuts against a neighbouring guide and stop element 62, 66. Since the piston rod 40 is rotatably locked during a dose dispensing, e.g. by means of the guide and stop element 62, 66 as well as by means of the axial guiding means in the form of resilient prong 76 and axial extending projection 60, an axial movement of the push-pull element 50 in distal direction is directly transferred to a corresponding distal displacement of the piston rod 40 and hence of the piston 18.

At the end of such a dose dispensing, distal displacement of the piston rod 40, its flange 44 abuts against a neighbouring guide and stop element 62, 66. Further the locking element 31 interlocks with an annular projection 46, 48 of the piston rod 40, which may be accompanied by an audible noise, indicating, that the end of a dose dispensing procedure has been reached. By this interlocking, the piston rod 40 is locked in both axial directions. The locking element 31 inhibits axial movement in proximal direction and the abutment of flange 44 and guide and stop element 62, 66 inhibit an axial movement in distal direction during dose setting.

The size of a dose, hence the amount of medicinal product to be dispense during dose dispensing is determined by the axial dimensions of the guide and stop elements 62, 66. In the embodiment according to FIGS. 1 to 18, the guide and stop elements 62, 66 vary in axial length and distance. Additionally or alternatively, the size of a dose can be determined by the axial distance 69 of neighbouring guide and stop elements 62, 66. Further, in order to have an appropriate interlocking of piston rod 40 and locking element 31, the axial distance of neighbouring annular projections 46, 48 of the piston rod 40 corresponds to the axial distance and/or size of the respective guide and stop elements 62, 66.

Figure 6:
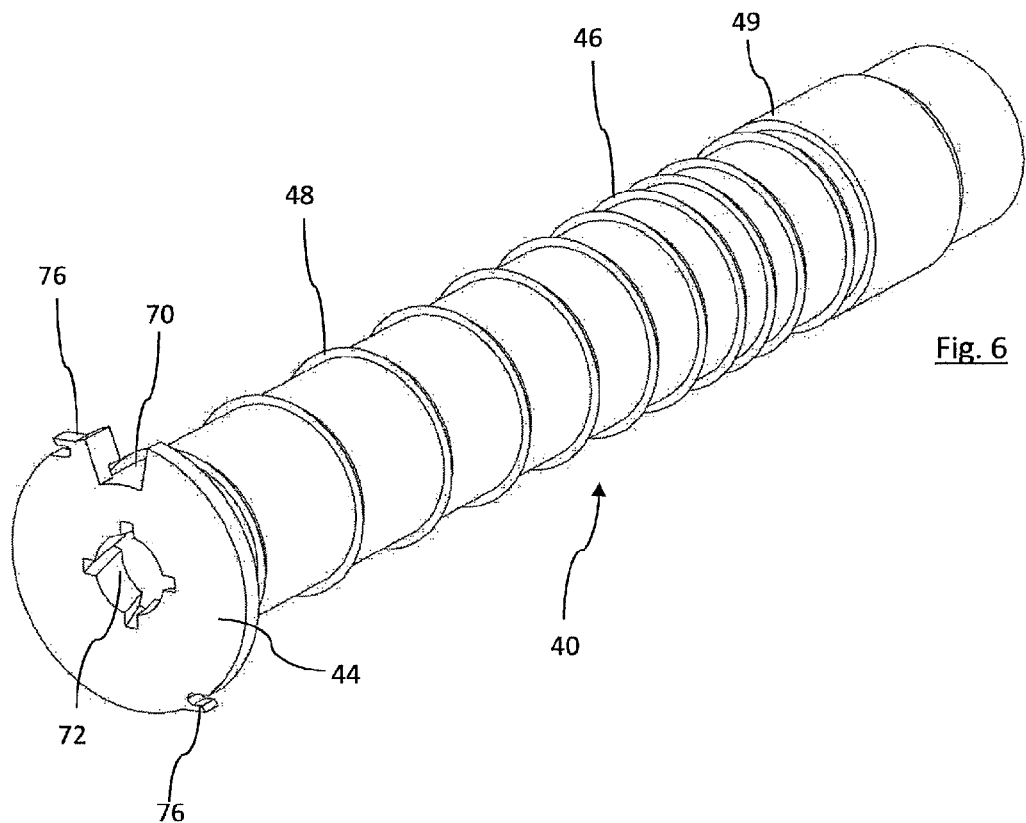
FIG. 6 depicts another perspective illustration of the piston rod as seen from its proximal end.

As can be further seen in FIGS. 4, 5 and 6, the axial distance 69 of neighbouring guide and stop elements as well as the axial distance between neighbouring circumferential annular projections 46, 48 of the piston rod 40 varies in axial direction. In this way, the size of consecutive doses may vary according to the pattern and design of guide and stop elements 62, 66 and respective annular projections 46, 48. With an increasing distance or size of guide and stop elements 62, 66 their relative angular offset at the inner surface of the guiding sleeve 30 may remain constant, in order to provide always the same rotational movement during dose setting, being accompanied by always the same translational movement of the push-pull element 50 in proximal direction.

In other embodiments, it is also conceivable, that the angular offset of consecutively arranged guide and stop elements 62, 66 varies with their axial size and/or with their mutual axial distance. This may lead to varying rotational movements of the piston rod during consecutive dose dispensing procedures accompanied by a corresponding varying translational movement of the push-pull element 50.

By making use of non-equidistant guide and stop elements 62, 66 and respective annular projections 46, 48, doses to be dispensed consecutively may vary in size according to a pre-defined dose dispensing scheme. In this way, a gradual or stepwise increase or decrease of the dose size can be provided by making use of an appropriate pre-defined pattern of guide and stop elements 62, 66 of a guiding sleeve 30. In this way, the end user does not have to manually set or select the dose size to be administered. The dose size is mechanically encoded in the guiding sleeve 30 and its corresponding piston rod 40.

In this way, a drug delivery device can be universally adapted to different dose dispensing schemes, only by making use of appropriate guiding sleeves 30 and piston rods 40. All other components of the drug delivery device 10 may thus remain unchanged. As can be further seen in FIGS. 3 and 4, the guiding sleeve 30 at its distal end comprises a last dose stop 63, which extends into a flange-like, radially inwardly protruding guiding element 65, being adapted to serve as axial and radial guiding means for the piston rod 40.

The last dose stop element 63 extends in distal direction right to the end of the guiding sleeve 30. When the last dose is dispensed, as illustrated in FIGS. 18a and 18b, the recess 70 of the piston rod's flange 44 still interacts with this last dose stop 63. In this way, the piston rod 40 remains rotationally locked, even after dose dispensing.

Due to this rotational locking and due to an optional additional axial locking by means of the locking element 31, another dose setting movement of the push-pull element 50 is inhibited. In this case, the entire drug delivery device 10 has to be disposed or refurbished.

The locking element 31 as illustrated in FIGS. 17a and 17b can be disposed between a socket of the housing component 20 and an annular end face of the guiding sleeve 30. The locking element 31 can be produced from metal. Alternatively, it can be integrally formed either with the guiding sleeve 30 or with the housing component 20. Guiding sleeve 30, housing component 20 as well as piston rod 40 are preferably made of a thermoplastic elastomer by making use of injection moulding processes.

Alternative to the illustrated embodiments, guiding sleeve 30 and housing component 20 can be manufactured as a single piece. However, by making use of a guiding sleeve 30 a larger degree of interoperability in view of various different dose dispensing schemes can be reached.

As further illustrated in FIGS. 5, 6, 17a and 17b, the piston rod 40 comprises a radially enlarged collar 49 at its outer circumference. In this way, the piston rod 40 can be radially fixed and radially centred even before the first dose has been set or dispensed. The proximal housing component 20 further has radially inwardly protruding ring-shaped guiding elements 27, as illustrated in FIG. 9, FIGS. 17a and 17b. As shown in FIGS. 17a and 17b, the piston rod 40 is radially guided in the housing 30 almost free from backslash at least before and eventually even after dispensing of a first dose.

In FIGS. 19, 20, 21a and 21b another, simplified embodiment of the invention is illustrated by making use of the same reference numerals as used in connection with FIGS. 1 to 18. For components having similar function or geometry the reference number has been incremented by 100.

In contrast to the embodiment of FIGS. 1 to 18, the simplified embodiment 100 comprises a piston rod 140 having equidistant and annular projections 148 of the same geometry. Correspondingly, the guiding sleeve 130 has identically shaped guide and stop elements 162 that form gaps of identical size.

Figure 21A:
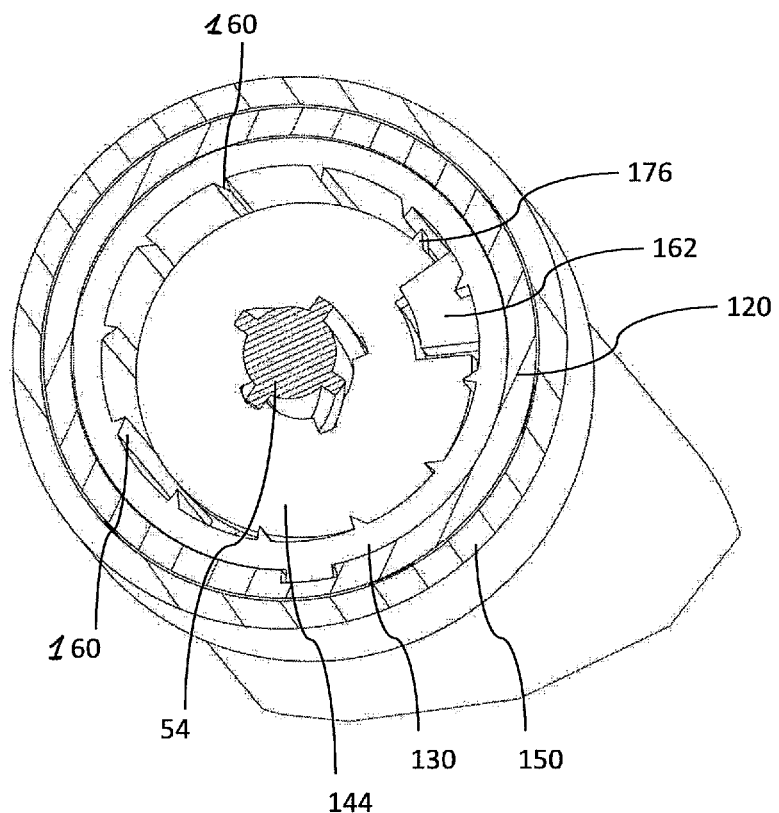
FIG. 21a depicts in a perspective cross sectional view the embodiment according to FIGS. 19 and 20 and FIG. 21b shows the configuration of FIG. 21a in a transverse cross section.
Figure 21B:
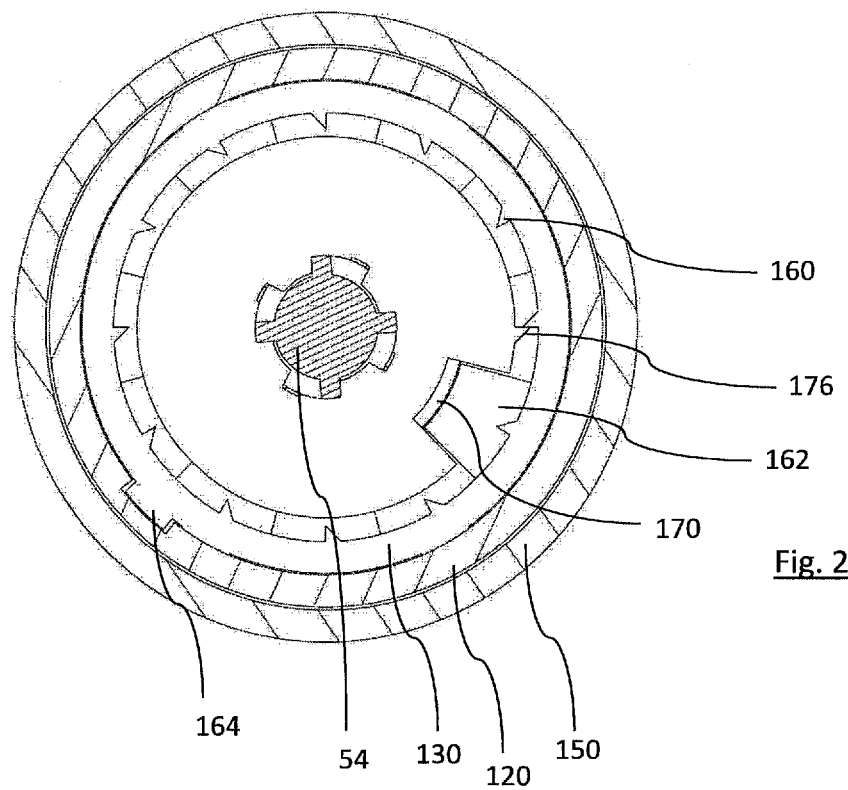

Instead of a resilient prong 76, the proximal flange 144 of the piston rod 140 near its recess 170 has a projection 176, having a triangular, saw-toothed shape, as illustrated in FIGS. 21a, and 21b. Projections 176 and projections 160 of the guiding sleeve 130 abut against each other in order to prevent unintentional rotation of the piston rod 140. Similar, as described in connection with the resilient prongs 76, the projections 176 allow for a unidirectional rotational movement of the piston rod 140. Generally, projections 176 and resilient prongs 76 are arbitrarily interchangeable.

A rotational locking between guiding sleeve 130 and proximal housing 120 is achieved by means of an axially extending protrusion 164. Additionally or alternatively, guiding sleeve 130 and housing 120 can be rigidly attached to each other by means of an adhesive, for example.

The push-pull element 150, as can be best seen in FIGS. 19 and 20, comprises a radially widened cylindrical portion 151 having radially protruding projections 154 that are guided in a respective groove 156 of the proximal housing component 120. Due to the equidistant arrangement of the guide and stop elements 162, the axial displacement of the push-pull element 150 is constant for each dose setting and dose dispensing action. Therefore, the axial length of the groove 156 can be designed accordingly.

The invention claimed is:

1. A drug delivery device for dispensing of a dose of a medicinal product, comprising:
    a housing having a proximal end and a distal end,
    a container comprising the medicinal product, a piston being retained in the container,
    a push-pull element, wherein the push-pull element is displaceable in proximal direction for setting of a dose and wherein the push-pull element is displaceable in distal direction for dispensing of a dose,
    a piston rod being coupled with the housing and having a distal end configured to abut and interact with the piston, the piston rod being further coupled with the push-pull element and is rotatable with respect to the housing when the push-pull element is displaced in the proximal direction,
    coupling elements for converting a proximal displacement of the push-pull element into a rotational movement of the piston rod and for converting a distal displacement of the push-pull element into an axial movement of the piston rod with respect to the housing such that the distal end of the piston rod pushes the piston distally within the container to dispense a dose, wherein the coupling elements comprise a recess and at least one guide and stop element.

2. The drug delivery device according to claim 1, wherein the coupling elements comprise an axially extending screw being rigidly coupled with the push-pull element and an inner thread of the piston rod being threadedly engaged with the screw.

3. The drug delivery device according to claim 1, wherein the piston rod is rotationally locked and moves axially in distal direction with respect to the housing during a displacement of the push-pull element in distal direction.

4. The drug delivery device according to claim 1, wherein the piston rod comprises a radially outwardly extending flange comprising the recess, the recess being matched with the at least one radially inwardly protruding guide and stop element disposed at an inner surface of the device.

5. The drug delivery device according to claim 4, wherein the radially inwardly protruding guide and stop element is disposed at the inner surface of a guiding sleeve fixed in the housing.

6. The drug delivery device according to claim 4, wherein the inner surface comprises a number of helically arranged radially inwardly protruding guide and stop elements.

7. The drug delivery device according to claim 6, wherein the radial arrangement and the axial size of the guide and stop element determine the size of a particular dose.

8. The drug delivery device according to claim 6, wherein the guide and stop elements are spaced at an axial distance being equal to or exceeding the axial size of the piston rod's flange.

9. The drug delivery device according to claim 4, wherein the piston rod's flange adjacent to its recess comprises a stopper extending axially in distal direction and being adapted to abut against a guide and stop element for delimiting a rotation of the piston rod.

10. The drug delivery device according to claim 4, wherein the piston rod's flange and the inner surface comprise mutually corresponding axial guiding means.

11. The drug delivery device according to claim 10, wherein the guiding means comprise a plurality of radially inwardly protruding and axially extending projections on the inner surface and at least one resilient prong on the piston rod's flange being adapted to interlock with the radially inwardly protruding projections for axially guiding the piston rod with respect to the housing.

12. The drug delivery device according to claim 1, wherein the piston rod comprises a plurality of annular retaining elements on its external circumference being axially spaced with respect to each other.

13. The drug delivery device according to claim 12, wherein the retaining elements are designed as circumferential protrusion and/or circumferential recess and comprise a saw-tooth profile.

14. The drug delivery device according to claim 1, further comprising a locking element disposed in the housing and being adapted to impede a displacement of the piston rod in proximal direction.

15. The drug delivery device according to claim 14, wherein the locking element is of disk-like or ring-like shape and comprises at least one radially inwardly protruding projection being adapted to interact with a corresponding retaining element disposed at the circumference of the piston rod.

* * * * *